United States Patent [19]

Kronvall

[11] Patent Number: 4,711,841
[45] Date of Patent: Dec. 8, 1987

[54] METHOD FOR DETERMINING ONE OR MORE ANTIGENS IN A SAMPLE

[75] Inventor: Hans C. G. Kronvall, Lund, Sweden

[73] Assignee: Pharmacia Aktiebolaget, Upsala, Sweden

[21] Appl. No.: 659,424

[22] Filed: Oct. 10, 1984

Related U.S. Application Data

[63] Continuation of Ser. No. 358,814, Mar. 16, 1982, abandoned, which is a continuation of Ser. No. 905,389, May 12, 1978, abandoned, which is a continuation of Ser. No. 647,269, Jan. 7, 1976, abandoned, which is a continuation of Ser. No. 409,560, Oct. 25, 1973, abandoned.

[30] Foreign Application Priority Data

Nov. 6, 1972 [SE] Sweden ............................ 14328/72
Feb. 8, 1973 [SE] Sweden ............................ 73017774

[51] Int. Cl.$^4$ .................... G01N 33/53; G01N 33/554
[52] U.S. Cl. ........................................ 435/7; 436/519; 436/828; 436/818
[58] Field of Search ............... 436/519, 531, 532, 533, 436/534, 805, 818, 828, 518; 435/882, 883, 884, 7

[56] References Cited

U.S. PATENT DOCUMENTS 3,873,684  3/1975  Fujita ..................................... 424/3
3,966,898  6/1976  Sjöquist et al. ................. 436/529 X
3,995,018  11/1976  Sjöquist .......................... 436/529 X

FOREIGN PATENT DOCUMENTS 2163318  9/1972  Fed. Rep. of Germany .

OTHER PUBLICATIONS

Lind, I. et al., *Acta Path Microbiol. Scand.*, Sect. B, vol. 80, 1972, pp. 281-291.

*Primary Examiner*—Sidney Marantz
*Assistant Examiner*—Jeremy M. Jay
*Attorney, Agent, or Firm*—Fred Philpitt

[57] ABSTRACT

A method for determining one or more antigens in a sample by immunological reaction between the antigen and antibodies directed specifically against the antigen in the presence of a liquid, said antibodies being bound to the surface of minute particles which are insoluble in the liquid in which the reaction is effected, the reaction leading to an agglutination which indicates the presence of the antigen in the sample. The antibodies are specifically fixed to a polypeptide which is derived from microorganisms and which can bind the Fc-part of the antibodies and the polypeptide is bound to the surface of the minute particles.

11 Claims, No Drawings

METHOD FOR DETERMINING ONE OR MORE ANTIGENS IN A SAMPLE

RELATED APPLICATIONS

The present application is a continuation of Application Ser. No. 358,814 filed Mar. 16, 1982 (now abandoned), which in turn is a continuation of Ser. No. 905,389 filed May 12, 1978 (now abandoned), which in turn is a continuation of Ser. No. 647,269 filed Jan. 7, 1976 (now abandoned) which in turn is a continuation of Ser. No. 409,560 filed Oct. 25, 1973 (now abandoned).

The present invention relates to a method for determining one or more antigens in a sample by an immunological reaction between the antigen or antigens and antibodies specifically directed against the antigen or antigens in the presence of a liquid, said antibodies being bound to the surface of small particles which are insoluble in the liquid in which the reaction is effected, said reaction leading to an agglutination which indicates the presence of the antigen or antigens in the sample. By "determination" is meant here and in the claims both qualitative determination (e.g. for identification) and quantitative determination.

Such methods are previously known. They can be used for determining both the antigen in solution and the antigen seated on the surface of minute particles such as bacteria bodies or virus particles. An example of determinations which can be carried out according to this principle is the establishment of the occurrence of human choriongonadotropin (HCG) in body fluids from women suspected of being pregnant. Another example is the typing of bacteria, e.g. in conjunction with diagnosing infectious illnesses.

The present invention is mainly characterized in that the antibodies have been specifically fixed to a polypeptide from microorganisms, the polypeptide being capable of binding the Fc-part of the antibodies, and in that the polypeptide is bound to the surface of the small particles.

The term "polypeptide" as used here and in the claims also relates to proteins, which as known are polypeptides, and the polypeptide may contain carbohydrate units.

The method of the present invention affords considerable advantages. Thus, it is possible to obtain a very high density of antibodies on the surface of the particle, the antibodies having their antigen binding parts (Fab-parts) extending outwardly from the particle, so that an effective binding with the antigen in question can take place. In this way, the agglutination obtained can be readily observed and indicated. In addition hereto, it is readily relatively simple to produce the particulate reagent material. One and the same material having polypeptides from microorganisms seated thereon, which polypeptide can specifically bind the Fc-part in the antibodies (hereinafter designated polypeptide (I) ), can be used for preparing reagents for determining different antigens since antibodies specifically directed against these antigens can be readily fixed via Fc-structures to the particle material. (The aforementioned antibodies are hereinafter designated antibodies (II).)

Polypeptide (I) is a polypeptide derived from microorganisms, e.g. from bacteria, and having the aforementioned properties. A particularly suitable example of polypeptide (I) in accordance with the above is the so called protein A from Staphylococcus aureus or fragments thereof, said fragments being of a polypeptide nature and being capable of binding the Fc-part in the aforementined antibodies. Another example is polypeptide from Staphylococcus epidermidis. Polypeptides from some strains of Streptococcus pyogenes (e.g. group A and C) may also be mentioned as polypeptides capable of reacting with the Fc-part of certain immunoglobulins. In this connection polypeptide (I) (e.g. protein A or the aforementioned fragments) can be bound to the surface of the bacteria bodies which produce the polypeptide, thereby affording a particularly simple method of producing reagent material for the method.

A particularly suitable embodiment of the method according to the invention is characterized from the basis of the above in that the particles to which the polypeptide capable of specifically binding the Fc-part in the antibodies is bound are bacteria bodies. The bacteria bodies may be staphylococcae, preferably killed staphylococcae.

In accordance with the invention, the polypeptide from microorganisms and capable of binding the Fc-part in the antibodies (II) may be so-called protein A, for example from Staphylococcus aureus or Staphylococcus epidermidis or Streptococcus pyogenes group A and C.

In accordance with the invention the polypeptide from microorganisms and capable of binding the Fc-part in the antibodies may be bound to minute particles of a polymer which is insoluble in the liquid in which the immunochemical reaction is effected. Examples of such polymers are gel particles containing copolymers of polyhydroxy compounds with bifunctional substances, e.g. the copolymer from dextran and epichlorohydrin (Sephadex ®) gel particles containing acrylates etc. The minute particles of polymers insoluble in the liquid in which the reaction is effected may, however, be swellable in the liquid.

In accordance with the invention, the polypeptides (I) capable of binding the Fc-part in the antibodies may be bound to the surface of the minute particles by means of covalent bonds.

In accordance with the invention, the polypeptide capable of binding the Fc-part of the antibodies may be bound to the surface of the minute particles by adsorption.

According to another feature of the invention, the bacteria bodies may as polypeptides (I) capable of binding the Fc-part of the antibodies contain a polypeptide derived from the bacteria (e.g. protein A or fragments thereof), the polypeptide being bound to the surface of the bacteria bodies by natural bonds between the polypeptide and said bodies and/or by a bond produced synthetically.

In accordance with another feature of the invention, the bacteria bodies with polypeptide (I) capable of binding the Fc-part in the antibodies seated thereon may be treated with an aldehyde, e.g. formaldehyde or glutaraldehyde.

In accordance with another feature of the invention, the bacteria bodies having seated thereon a polypeptide (I) capable of binding the Fc-part in the antibodies may be treated with heat to kill and/or sterilize said bacteria bodies.

In accordance with a further feature of the invention, the antibodies which are specifically fixed to the polypeptide capable of binding the Fc-part of said antibodies may be bound to the polypeptide by covalent bonds.

These bonds may be produced, for example, with the assistance of glutaraldehyde or cyanogen bromide after the antibodies have been specifically fixed to the polypeptide (I).

In accordance with the invention the antigen and/or antigens to be determined may, for example, be bacteria antigen. The antigen or antigens may be capsule antigens from bacteria. According to the invention, the antigen or antigens to be determined may be, for example, a virus antigen. They may also be, for example, of human or animal origin. The antigen or antigens may be present in solution, irrespective of their source. According to the invention, the antigen or the antigens to be determined may be bound to minute particles such as the bacteria or virus which produced them.

In accordance with another feature of the invention, the minute particles to which the polypeptide (I) capable of binding the Fc-part of the antibodies is bound may be coloured to facilitate observation of the agglutination.

The invention also embraces the case when the aforementioned method is applied to diagnose of physiological or pathological conditions with humans or animals in which an antigen or antigens is involved, a sample which may contain the antigen or antigens being brought into contact with specific antibodies which are bound to the surface of minute particles, an agglutination being obtained if the sample contains the antigen or antigens. The method is mainly characterized in that antibodies are used which are specifically fixed to a polypeptide from microorganisms, said polypeptide being capable of binding the Fc-part therein, and in that the polypeptide is bound to the surface of the minute particles.

In accordance with another feature of the invention, the pathological or physiological condition in which the antigen or antigens is involved may, for example, be caused by an illness, e.g. an infectious illness. In accordance with the invention, the physiological condition in which the antigen or antigens is or are involved may be the result of a pregnancy for example.

The determinations may also be effected as quantitative determinations in a manner conventional with agglutination methods, e.g. by testing a series of different degrees of dilution of the sample and comparing the result with an analogous test with a sample of known concentrations of the antigen in different states of dilution. In this way, the most diluted solution which nevertheless results in agglutination can be established.

As mentioned above, the agglutination test is carried out in the presence of a liquid. In general there is normally selected an aqueous liquid, e.g. a buffered physiological common salt solution having a suitable pH.

The sensitivity level of the test can be controlled by varying the reagent material and the test conditions.

Particulate material having seated thereon polypeptide (I) and antibodies (II) specifically fixed to polypeptide (I) can be prepared in the following manner: Bacteria bodies having polypeptide (I) seated on the surface thereof may be killed under mild conditions, e.g. by treating same with formaldehyde or glutaraldehyde and then subjecting the same to short duration heat treatment. Polypeptide (I) is also bound more firmly to the bacteria bodies in this way. Alternatively, polypeptide (I) can be bound to polymer particles, e.g. by reacting the same with cyanogen bromide and then with polypeptide (I) in a manner known with the binding of other polypeptides to polymer particles. The particles with polypeptide (I) seated thereon are then contacted with a solution containing antibodies (II), the Fc-part of which can be specifically fixed to polypeptide (I). (Examples of such antibodies (II) are antibodies belonging to the IgG-class from animals, e.g. from rabbits which show very little tendency towards self-agglutination of the particles. The Fc-parts of these antibodies and protein A as example of polypeptide (I) reacts specifically with each other, the antibodies (II) being specifically fixed to polypeptide (I) via their Fc-parts.) In this way the antibodies (II) are bound via their Fc-fractions to polypeptide (I). The particulate material is then washed. Thus, there is obtained a particulate material on which the antibodies (II) are seated secured by their Fc-parts while the Fab-parts are intact and can bind the antigen or antigens in question.

It is known to the art that reagents for the purpose in question consisting of minute particles having antibodies bound thereto in aqueous suspension sometimes have a certain tendency towards self-agglutination. The person skilled in the art is, however, capable of avoiding false results due to such self-agglutination by selecting suitable conditions for the test such as suitable dilutions of the reagent material and the sample and by selecting antibodies from suitable animal species. Such conditions can be determined readily by usual pre-tests.

The invention will now be described with reference to a number of examples.

EXAMPLE 1

Preparation of reagent material

Staphylococcus aureus, strain Cowan I, is cultivated in 500 ml CCY-medium (see Arvidsson et al. Acta Path. Microbiol. Scand. Seet B, 79 (1971), page 399) in shake culture at 37° C. for 24 hours. The bacteria were separated from the culturing medium by centrifugation and were washed twice in a physiological common salt solution and then slurried up in 250 ml of 0.5% formaldehyde in a phosphate buffered common salt solution (0.15 M NaCl, 0.01 M sodium phosphate pH 7.4) in water. After being stirred for 3 hours at room temperature the bacteria were separated from the formaldehyde solution by centrifugation and washed 4 times in a physiological common salt solution and then centrifuged.

A physiological common salt solution containing 0.1% of sodium azide and being nine times greater than the volume of the packed staphylococcae was added thereto. The 10% suspension of bacteria bodies covered with the protein A naturally occurring on these bacteria was pumped at a rate of 500 ml per hour through a 190 cm long metal tube having an inner diameter of 4 mm, and an outer diameter of 5 mm, which was kept lowered into a water bath at a temperature of 80° C., and was then pumped through a similar pipe submersed in 4° C. water for cooling the suspension. The thus heat-treated staphylococcae suspension was then centrifuged, the bacteria bodies slurried in the buffer and centrifuged again and then slurried to a 10% suspension in said buffer. Admixed with 1 ml of the suspension was 0.1 ml of antiserum having antibodies specifically directed against the antigen or antigens to be determined, for example pneumococcae-typing serum from rabbits (e.g. from Statens Seruminstitut, Copenhagen). Subsequent to being mixed, the antibody-coated bacteria were washed after a few minutes with a buffer (containing 0.1% sodium azide, 0.15 ml NaCl, 0.2% gelatin, 0.01M sodium phosphate in water, pH 7.4) and were then slurried in 10 ml of said buffer.

EXAMPLE 2

Typing of bacteria

Typing of pneumococcae in accordance with the aforementioned principle is carried out in accordance with the following. In this connection there were used the reagents particles produced in accordance with example 1, the particles in this case being covered with antibodies specifically directed to type specific pneumococcus antigens obtained by immunizing rabbits. Two drops of the reagent liquid were placed on a lense glass and a small sample of the pneumococcus strain to be examined taken with a platinum eye was suspended in the reagent. The mixture was inspected for 1-3 minutes while rocking the same and the occurrence of agglutination was observed. Agglutination indicates that the pneumococcus in question is of the type against which the antibodies and therewith the reagent is directed.

EXAMPLE 3

Determining soluble antigens

The example is intended to show the occurrence of soluble antigen, namely bovine serum albumin and human gammaglobulin in physiological common salt solution containing 1 mg, 0.1 mg and 0.01 mg of said proteins per ml. Added to two droplets of the solution to be tested were two drops of reagent obtained according to example 1, i.e. containing particles coated with antibodies specifically directed against the antigen or antigens to be determined. The droplets were thoroughly mixed and inspected for the possible occurrence of agglutination. Agglutination occurred in all cases when the sample contained the antigen against which the Fab-part of the antibodies in the reagent was directed. Tests were also carried out with other protein solutions, but no agglutination was obtained.

EXAMPLE 4

Detection of human choriogonadotropin (HCG)

Solutions of human choriongonadotropin (HCG) containing 500,000, 50,000, 5000, 500 and 50 IE per liter were tested with a reagent produced in accordance with example 1 and containing particles coated with antibodies (formed in rabbits) directed against HCG. To two drops of test solution were added two drops of the reagent suspension. Agglutination occurred when testing the concentration of 5000 IE per liter and higher. No agglutination was obtained with solutions of 500 and 50 IE per liter under the test conditions in question. In a corresponding manner urine samples taken from women were tested. Agglutination was obtained with some of the samples taken from pregnant women, but not with the urine taken from women who were not pregnant.

EXAMPLE 5

Preparation of reagent material with coloured particles

To 10 ml of a 1 percent suspension of the particulate material from example 1 in the same phosphate buffer were added 100 μl of an Amidoschwartz-solution containing 10 mg of the dyeing agent per ml. The suspension was well mixed with the dye, wherewith the bacteria bodies were coloured. The suspension can either be used directly or subsequent to being washed and re-slurried in the phosphate buffer.

The coloured reagent material can be used, for example, in the manner described in examples 2, 3 and 4.

Colouring of the particles facilitates observation of the agglutination.

EXAMPLE 6

Preparation of reagent material

Streptococci with high contents of Fc-reacting surface protein may also be used as particles according to the following procedure. Streptococcus pyogenes, strain group A (No. 235 Kronvall) is cultured in 1000 ml of Todd-Hewitt broth while stirring slightly at 37° C. for 24 hours. The bacteria are then separated from the medium by centrifugation, washed once in phosphate buffered common salt solution and slurried in 0.5% formaldehyde in the same buffer. After stirring for 3 hours at room temperature the bacteria are washed 3 times in phosphate buffered common salt solution and slurried in the same buffer with the addition of 0.02% sodium azide to a concentration of $10^{10}$ bacteria per ml. To 6 ml of this suspension 0.1 ml of antiserum, for instance pneumococcus typing sera (from rabbit) is added and the mixture is centrifugated after 15 minutes at room temperature. The streptococci which are now covered with antibodies are then washed with a buffer and slurried in 10 ml of phosphate buffered common salt solution containing 0.02% sodium azide. The reagent material may be used in a way similar to that described above.

What I claim is:

1. A method for testing for the presence of a suspected specific antigen in a biological specimen of animal origin, comprising the step of combining the specimen containing the suspected antigen with a protein-A-containing, microbial cell suspension sensitized with an IgG antibody specific to the suspected antigen so that the Fc-part of the antibody is attached to protein A which in turn is attached to the microbial cell, whereby agglutination occurs if the test is positive, said antibody showing substantially no tendency toward self-agglutination of the microbial cells.

2. In an agglutination test for determining an antigen in a liquid sample by an immunological reaction between the antigen and antibodies directed specifically against the antigen, said antibodies being bound to the surface of bacteria which are insoluble in the liquid sample, said reaction leading to agglutination indicating the presence of the antigen in the sample, the improvement comprising said bacteria having their protein A fixed on the surfaces thereof and the Fc-parts of said antibodies specifically fixed to said protein A, said antibody being a rabbit antibody specific to the suspected antigen belonging to the IgG class and showing substantially no tendency toward self-agglutination of the bacteria.

3. A method according to claim 2 wherein the bacteria are protein A producing Staphylococci.

4. In an agglutination test for determining an antigen in a liquid sample by an immunological reaction between the antigen and antibodies directed specifically against the antigen, said antibodies being bound to the surface of bacteria which are insoluble in the liquid sample, said reaction leading to agglutination indicating the presence of the antigen in the sample, the improvement comprising said bacteria are killed protein A producing Staphylococci bacteria having their protein A fixed on the surfaces thereof and the Fc-parts of said antibodies are specifically fixed to said protein A, said antibodies being specific to the suspected antigen and belonging to the IgG-class and showing substantially no tendency toward self-agglutination of the bacteria.

5. A method according to claim 4 wherein the staphylococci bacteria are protein A producing Staphylococcus Aureus Aureus.

6. A method according to claim 4 wherein the antigen is a bacterial antigen.

7. A method according to claim 6 wherein the bacterial antigen is a capsule antigen.

8. A method according to claim 4 wherein the antigen is of animal origin.

9. A method according to claim 4 wherein the antigen is in dissolved form.

10. A method according to claim 6 wherein the bacterial antigen is bound to the bacteria which produced it.

11. A method according to claim 4, wherein the bacteria are colored to facilitate observation of the agglutination.

* * * * *